United States Patent
Moskal

(10) Patent No.: US 10,340,035 B2
(45) Date of Patent: Jul. 2, 2019

(54) MEDICAL RECORD STORAGE WITH ELECTRONIC SIGNATURE

(71) Applicant: Fenwal, Inc., Lake Zurich, IL (US)

(72) Inventor: Witold Moskal, Park Ridge, IL (US)

(73) Assignee: Fenwal, Inc., Lake Zurich, IL (US)

(*) Notice: Subject to any disclaimer, the term of this patent is extended or adjusted under 35 U.S.C. 154(b) by 690 days.

(21) Appl. No.: 14/079,213

(22) Filed: Nov. 13, 2013

(65) Prior Publication Data

US 2015/0134359 A1    May 14, 2015

(51) Int. Cl.
*G06F 19/00* (2018.01)
*G06F 21/62* (2013.01)
*G16H 10/60* (2018.01)
*G06F 21/41* (2013.01)

(52) U.S. Cl.
CPC ............ *G16H 10/60* (2018.01); *G06F 19/00* (2013.01); *G06F 21/41* (2013.01); *G06F 21/6245* (2013.01)

(58) Field of Classification Search
CPC ......... G06F 21/6227; G06F 2221/2101; G06F 16/81; G06F 16/24573; G06F 16/8373; G06F 21/64; G06Q 50/22; G06Q 50/24; G16H 50/20
See application file for complete search history.

(56) References Cited

U.S. PATENT DOCUMENTS

| | | | |
|---|---|---|---|
| 7,962,348 B2 | 6/2011 | Dew et al. | |
| 7,983,930 B1* | 7/2011 | Romans | 705/2 |
| 2005/0216311 A1 | 9/2005 | Gmelin et al. | |
| 2009/0210250 A1 | 8/2009 | Prax et al. | |
| 2010/0017223 A1 | 1/2010 | Johnson et al. | |
| 2010/0198608 A1* | 8/2010 | Kaboff et al. | 705/2 |
| 2012/0086971 A1* | 4/2012 | Bisbee | H04L 9/321 358/1.14 |
| 2013/0006666 A1 | 1/2013 | Schneider et al. | |
| 2013/0190674 A1* | 7/2013 | Case | A61M 5/1723 604/6.01 |

* cited by examiner

*Primary Examiner* — Maroun P Kanaan
(74) *Attorney, Agent, or Firm* — Becker Patent Law, LLC

(57) ABSTRACT

A server computer for storing an electronic medical record with an electronic signature in a database has a network interface circuit and a processing circuit. The network interface circuit is configured to provide communications over a network. The processing circuit is configured to receive an electronic medical record and store the electronic medical record in the database in compliance with at least one record storage criterion. After storing the electronic medical record in the database in compliance with the at least one record storage criterion, the processing circuit is configured to receive an electronic signature for the electronic medical record and store the electronic signature in association with the electronic medical record in the database.

4 Claims, 4 Drawing Sheets

MEDICAL RECORD STORAGE WITH ELECTRONIC SIGNATURE

BACKGROUND

The present application relates generally to the storage of medical records with electronic signatures.

An electronic record is used to store information in digital format. The format of the record may vary from system to system. There are number of advantages of electronic over printed records, especially when applied to medical devices, including: accuracy of information, flexibility of storage in terms of physical space, effectively instantaneous availability to access and easiness of transfer between different homogenous and heterogeneous systems.

In addition, electronic records offer the possibility to be electronically signed off to make them equivalent to conventionally signed paper records. Electronic signatures have a variety of formats including biometrics (e.g. fingerprints) and a combination of at least two identifications (e.g. a pair of user name and password). Electronic signatures can be used to acknowledge approval of electronic records.

In the medical devices field, electronic records and electronic signatures are regulated by corresponding regulatory bodies for specific geographic regions of the globe. High level requirements of electronic records and electronic signatures can include the following: (1) safe and secure long term storage of records; (2) accessibility of stored records to regulatory audits upon request; (3) assurance of data integrity between source and storage of the record; and (4) security of access to stored data. Systems intending to claim compliance with regulations of electronic records and electronic signatures are directed to satisfying one or more of these requirements.

DETAILED DESCRIPTION OF ILLUSTRATIVE EMBODIMENTS

Figure 1:
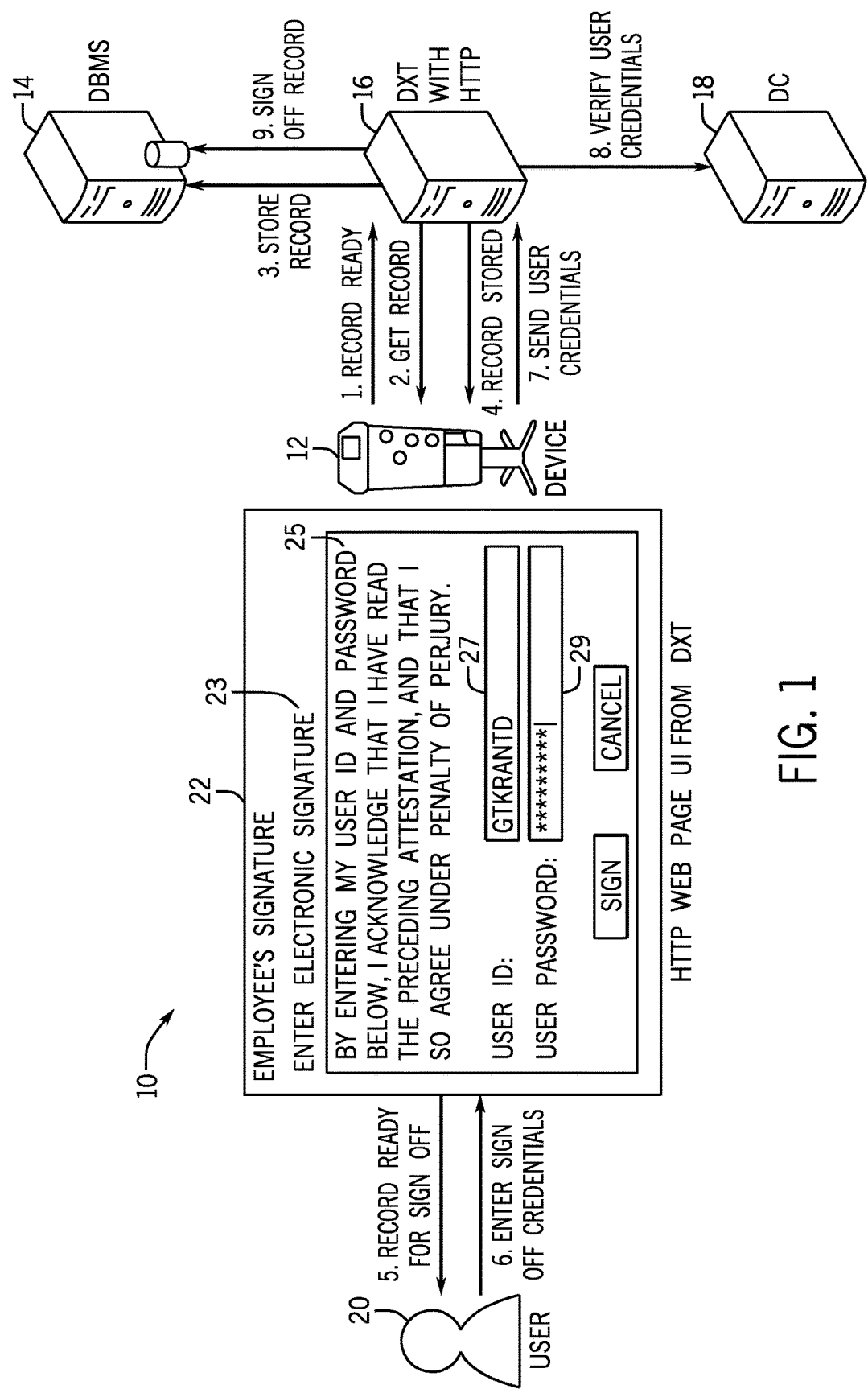
FIG. 1 is a flow diagram of a system for storing an electronic medical record with an electronic signature, according to an illustrative embodiment.

One or more embodiments described herein may locate long term storage of medical records and electronic signatures outside of or in a different location than the record source, in the case where the record source is an embedded processor in a medical device. Locating long term storage on a device other than the embedded device may be more cost effective, may provide for flexibility of physical storage, may provide improved security of the information, and/or may improve ease of maintenance of the record.

One or more embodiments described herein may pass a received medical procedure record to a database as it is received from the medical device or instrument.

On or more embodiments described herein may provide a client-server model for a user interface at the medical device, where the medical device is a client to a remote server. Use of a hypertext transfer protocol (HTTP) web page served from the remote server to the medical device can offer flexibility to changes without affecting implementation of the medical device software.

One or more embodiments may reduce development and verification effort as only one system component will be required to change, when user interface requirements change.

One or more embodiments may offer runtime flexibility of the user interface to be executed either at the medical device or with another web enabled device (e.g. laptop computer, tablet, smart phone, etc.).

One or more embodiments may provide for aggregation of data from multiple embedded devices into a single point of access to enable abstract access to data of heterogeneous embedded devices through a common user interface to a single database management system (DBMS).

One or more embodiments may provide for application of the electronic signature to the electronic record after it has been securely stored into the long term storage, thus eliminating risks associated with transmission or storage failures of the source embedded device.

One or more embodiments may provide flexibility to the implementation of where the electronic signature is applied. For example, the source embedded device can act as user interface for the electronic signature so that no additional system components are required. At the same time, the user interface can be displayed on a networked portable computing device (e.g. laptop, tablet or smart phone).

One or more embodiments may provide access from external systems to stored records which are fully compliant with applicable governmental regulations, rather than records in the form of transient data with limited storage duration. This may enable external systems (e.g. Donor Management Systems) to access data in an on-demand mode thus reducing need for transferring data that may not be required, i.e. accessing only partial record.

One or more embodiments may provide for backup of electronically signed medical records in accordance with at least one record storage criterion in a central location for multiple devices, to avoid the need for compliant backup storage devices at each medical device in a facility. For example, a database may receive medical records from at least two different care areas (e.g., an intensive care unit, a primary care unit, a clinic, etc.) within an environment.

Referring now to FIG. 1, a system 10 for the storage of an electronic medical record with an electronic signature is shown. In this embodiment, system 10 is illustrated as being used with a medical device 12 for performing a medical procedure on a patient, such as an apheresis machine. An apheresis machine is a machine configured to provide extracorporeal therapy to a patient by removing the patient or donor's blood, separating out one or more constituents of the blood (e.g., red blood cells, white blood cells, plasma, etc.), and returning the remaining constituents to the patient. A centrifuge device may be used for the separation. Exemplary apheresis devices include the Amicus separator, Alyx component collection system, Autopheresis-C system, and Aurora Plasmapheresis system, all manufactured by Fenwal, Inc., a Fresenius Kabi Company, Lake Zurich, Ill. In alternative embodiments, components or features of system 10 may be used with other medical devices, such as infusion pumps, patient monitors, medical imaging machines, etc., and/or with other computing devices.

Medical device 12 is configured to generate data relating to a medical procedure implemented on a patient. Device 12 is further configured to generate an electronic medical record for the patient. An electronic medical record may contain a patient identifier, such as the patient's name, and other data about the procedure performed on the patient, such as the type of procedure performed, the result or yield from the procedure, etc. According to one embodiment, long term storage of the medical record is implemented on a database 14. Database 14 may be a DBMS hosted on a server host platform, such as Microsoft Windows XP, Microsoft Windows Server 2008, etc., rather than in the embedded device environment of medical device 12, which can significantly reduce the cost of implementation and improve system availability and maintenance. An embedded processor refers to a processor with a dedicated function within a larger mechanical or electronic device and is contrasted with a general-purpose computer, such as a personal computer (PC).

In this embodiment, a server computer 16 is configured to perform steps in the system and method for storing the electronic medical record with an electronic signature in database 14. Further, server computer 16 uses a credential verification server computer 18. In alternate embodiments, devices 14, 16 and 18 may be implemented on a single server computer, a plurality of server computers, a server farm, a cloud server environment, or using other computer resources. Devices 14, 16 and 18 may comprise analog and/or digital circuit components forming a processing circuit configured to perform the steps described herein. The processing circuit may comprises discrete circuit elements and/or programmed integrated circuits, such as one or more microprocessors, microcontrollers, analog-to-digital converters, application-specific integrated circuits (ASICs), programmable logic, printed circuit boards, and/or other circuit components. One or more of device 14, 16 and 18 each may comprise a network interface circuit configured to provide communications over one or more networks with each other and/or with medical device 12. The network interface circuit may comprise digital and/or analog circuit components configured to perform network communications functions. The networks may comprise one or more of a wide variety of networks, such as wired or wireless networks, wide area-local-area or personal-area networks, proprietary or standards-based networks, etc. The networks may comprise networks such as an Ethernet network, networks operated according to Bluetooth protocols, IEEE 802.11x protocols, cellular (TDMA, CDMA, GSM) networks, or other network protocols. The network interface circuits may be configured for communication of one or more of these networks and may be implemented in one or more different sub-circuits, such as network communication cards, internal or external communication modules, etc.

FIG. 1 also illustrates a user 20, who may be a clinician, such as a doctor, nurse, or other medical professional authorized to electronically sign a medical record for the patient. An electronic signature user interface 22 is illustrated, provided on a display of medical device 12 in this illustrative embodiment, which will be described in greater detail below.

Figure 2:
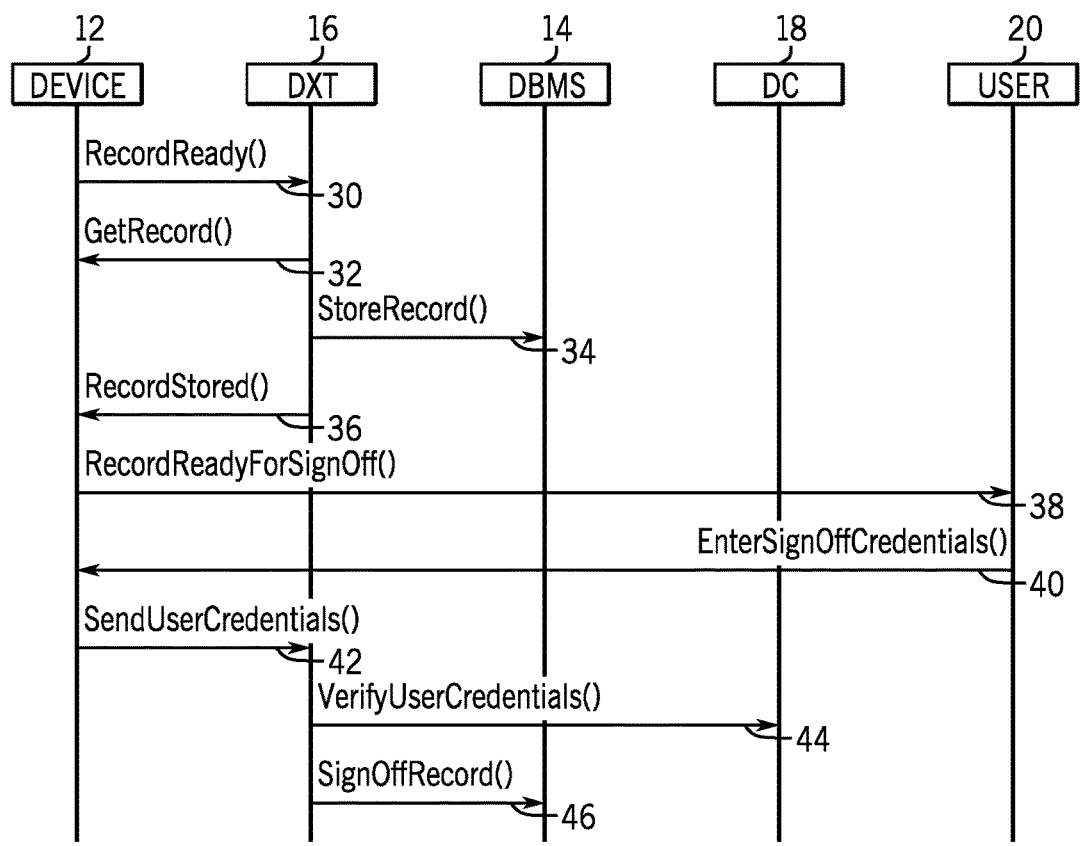
FIG. 2 is a sequence diagram illustrating a messaging method using the system of FIG. 1.

Referring now to FIG. 2, a sequence diagram will be used to illustrate a system and method for storing an electronic medical record with an electronic signature, according to an illustrative embodiment. While shown in a time sequential order from top to bottom, the steps or message transmissions illustrated may, in alternative embodiments, be rearranged in different orders. At a step 30, server 16 is configured to receive a record ready message from device 12 indicating that device 12 has an electronic medical record read for processing (e.g., storage) by server 16. The message may be sent asynchronously and/or at the end of a medical procedure performed by device 12, or at other synchronous or periodic times, such as once per hour, once per day, etc. Further, the message may be sent in response to a request from server 16 or the message may be pushed without requiring a request. Server 16 may be configured to poll device 12 at a predetermined frequency, such as at least once every 500 milliseconds. At a step 32, server 16 is configured to transmit a get record message to device 12 to request a copy of the medical record. At a step 34, server 16 is configured to receive the electronic medical record over a network from device 12 and to store the record in database 14. The storage of the record may be in compliance with at least one record storage criterion, as will be described in greater detail below.

At a step 36, server 16 is configured to send a record storage message to device 12 to notify device 12 of a successful record storage in database 14 in accordance with the at least one record storage criterion. At a step 38, a record ready for storage function is run by device 12 to present a user interface to user 20 for facilitating an electronic signature of the record. At a step 40, sign off credentials are received from user 20 (e.g., a username and password, or other credentials, such as a digital certificate, etc.). At a step 42, the user credentials are sent to and received by server 16. At a step 44, user credentials are verified by transmitting them to verification server 18. If the credentials are valid, at a step 46, server 16 is configured to store the sign off record or electronic signature in database 14 in association with the electronic medical record stored there at step 34.

In one embodiment, server 16 is configured to receive the electronic signature for the electronic medical record (at step 42) after the electronic medical record is stored in database 14 in compliance with at least one record storage criterion (at step 34). Other events illustrated in FIG. 2 may be performed before or after these steps in this embodiment. By storing the medical record in database 14 in accordance with the record storage criterion before receiving the electronic signature from the user or medical device 12, security of the medical record is improved. For example, if the medical record is lost in transmission due to a technical error, it has not yet been electronically signed. Further, from the user's perspective, the user need not know that the medical record is already stored at the time the electronic signature user interface 22 is displayed, so as to avoid any confusion on the part of the user.

Record storage criteria may be any of a number of criteria relating to secure, reliable, retrievable, and/or validly stored records. For example, record storage criteria may comprise audit trail criteria, such as, a) a requirement that every change to a medical record be tracked and saved, or b) long-term storage criteria, such as a requirement to save a medical record for at least X years (e.g., 5 years, 10 years, 20 years, etc.). Record storage criteria may comprise security or privacy criterion, such as: a) a requirement that access is limited to certain individuals having suitable credentials, or b) a requirement that the DBMS automatically log-off a user after a predetermined period of inactivity. Record storage criteria may comprise verification criteria, such as a signature sequence required before a document is deemed properly electronically signed (e.g., multiple signatures required in a particular sequence). Record storage criteria may comprise an accessibility criterion, such as a requirement that the medical record be available for regulatory audits upon request. Record storage criteria may comprise a data integrity criterion, such as a requirement of a certain level of data integrity between a source computer and a destination computer. For example, a cyclic redundancy check (CRC) may be used. Record storage criteria may comprise a backup criterion, such as a requirement that data be backed up to a second storage device meeting predetermined data backup requirements. Record storage criteria may be enumerated in government regulations, such as FDA 21 CFR Part 11 governing electronic records and signatures or the European Commission, Annex 11 (Computerized Systems) to Volume 4 (Good Manufacturing Practice (GMP)—Medicinal Products for Human and Veterinary Use) of the Rules Governing Medicinal Products in the European Union (EudraLex). Other government regulations may provide similar or different record storage criteria. The one or more record storage criteria may provide a guarantee of security of the data in the DBMS 14.

In one embodiment, the medical record may be stored in database 14 in accordance with one or more record storage criteria before the user is presented with the user interface for electronic signature 22. In another embodiment, the user interface for electronic signature 22 may be provided during or before storage of the medical record in database 14 in accordance with the one or more record storage criteria. In another embodiment, the server 16 is configured to, after storing the electronic medical record in the database 14 in compliance with the at least one record storage criterion, transmit a notification (as in step 36) that causes a remote computing device (e.g., device 12 or another device) to request credentials for the electronic signature. The notification may be one of several criteria that need be satisfied before the credentials request takes place.

Electronic signing of the medical record may be done using a plurality of different mechanisms. In one example, a user interface screen 22 (FIG. 1) is generated by an embedded processor in device 12 using user interface data programmed in firmware or other non-volatile memory during manufacture or upgrade of device 12. In one embodiment, screen 22 comprises a prompt 23 informing the user 20 to enter credentials. An agreement or acknowledgment message 25 may also be displayed. Fields for credentials, such as a user ID field 27 and a user password field 29, are also provided. In alternative embodiments, other credentials may be requested, such as biometric data from a biometric sensor (e.g., fingerprint sensor, retinal scanner, microphone for a voice recognition device, etc.), or other credentials such as a personal ID number (PIN), digital certificate file provided from a memory, or other credentials.

Credentials entered may be transmitted by device 12 to server 16 for verification. In this embodiment, server 16 transmits the credentials to a domain controller 18 with established domain policies of the end user environment, for example using a Microsoft Active Directory server. In this case, domain controller 18 is a different server computer having a separate housing. Alternatively, the credentials may be verified on server 16 or using other credential verification tools, local or remote (e.g., over the Internet) relative to server 16.

Referring now to step 46, the verified credentials are used to generate an electronic signature on server 16 that is associated with and stored with the medical record stored at step 34. The electronic signature is generated by a user entering a signature on device 12 (step 40), device 12 sending the signature to server 16 (step 42), and server 16 verifying the signature against what is stored on DC 18 (step 44). Part of the signature that indicates who signed the record is stored on server 16.

At step 38, RecordReadyForSignoff( ) will specify a medical record by a unique identifier for that record. Then the EnterSignOffCredentials and SignOffRecord functions act on this uniquely identified record. The final, signed medical record is a function of the original record from device 12 plus the identity of the user who signed the record and a timestamp when the record was signed. In some embodiments, the identity and timestamp are not part of the record per se, but are associated with the record with an entity relationship, since one record can be signed off by more than one individual in sequence.

Figure 3:
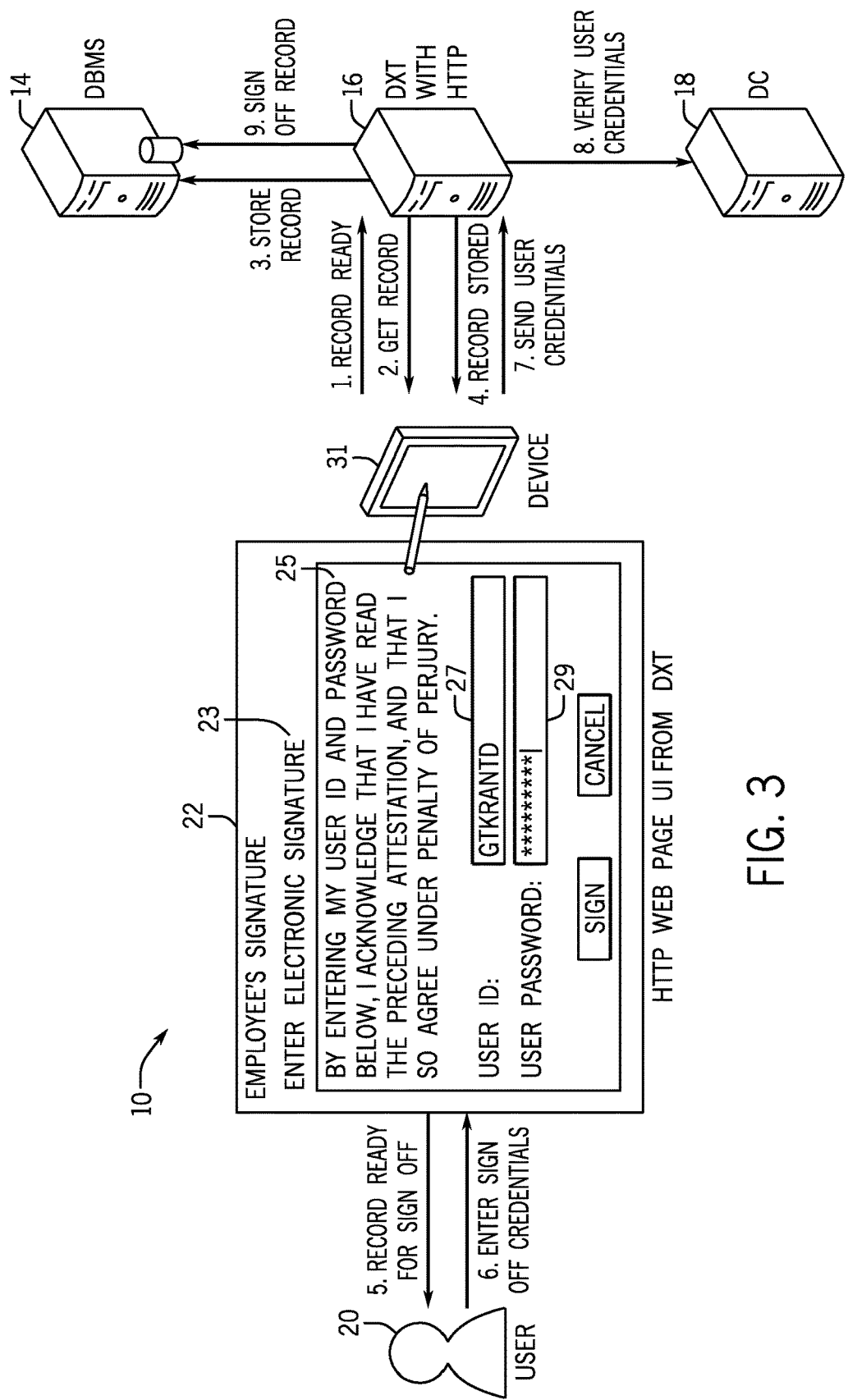
FIG. 3 is a flow diagram of a system for storing an electronic medical record with an electronic signature, according to another embodiment.

Referring now to FIG. 3, a system for storing an electronic medical record with an electronic signature according to another embodiment will be described. This embodiment has similar components to those in the embodiment of FIG. 2. In this embodiment, the electronic signature is received from any network-connected device and need not be received from medical device 12. In this manner, the system is distributed and an electronic signature user interface need not be provided on the medical device.

In this embodiment, server 16 is configured to receive an electronic medical record from a first computing device over the network, the first computing device being at least a portion of the medical device 12, for example at least partially within a housing of medical device 12. Server 16 may be configured to receive an electronic signature for the electronic medical record from a second computing device 31 over the network, wherein the first computing device 12 and second computing device 31 are distinct computing devices each having their own housings. In one example, first computing device 12 may have an embedded processor and second computing device 31 may be a general-purpose computer. Second computer 31 may be a desktop computer or a portable computer, such as a laptop, tablet computer, smartphone, personal digital assistant, etc. A tablet computer is typically larger than a smartphone, for example at least seven inches measured diagonally. Second computer 31 may have a housing configured to be held in a person's hand while being used. The second computer may have a touch screen interface and may further have a cellular phone processor, Wi-Fi transceiver, digital camera and/or other portable computing features. The electronic signature or other credentials may be entered by the user using a hard keyboard integrated with the housing of the second computer or a soft keyboard implemented by the touch screen interface. A stylus or other touching device may be used.

Programming for the second computing device to implement the credential input or electronic signature features may be provided as a downloadable application operable on second computer 31. The application may be downloaded from an application store operated by a manufacturer of the phone or the phone's operating system. The application may alternatively be downloaded via an e-mail message, text message comprising a link with a uniform resource locator pointing to a network address, via a universal serial bus memory device, or by other mechanisms. The application may alternatively be programmed into device 31 during manufacture, for example in an embodiment in which device 31 has an embedded processor and device 31 is manufacturer for the specific purpose of collecting and transmitting credentials to server 16. In another embodiment, device 31 may comprise a web browser or other user interface configured to receive a web page or other user interface code wirelessly from a network location on the Internet. In one example, server 16 may serve the web page providing the user interface for collecting user credentials for verification.

In another embodiment, server 16 may be configured to generate a user interface screen configured to receive an electronic signature for the medical record, transmit the user interface screen to the medical device over the network and receive an electronic signature entered using the user interface screen. For example, the user interface screen may be a web page based on HTTP served from server 16 to medical device 12 using a TCP/IP protocol. The web page may be accessed using a web browser or other code operable on medical device 12. The web browser may navigate, using a pre-stored or user-entered uniform resource locator, to a network location, which may be a secure HTTP site. The network location may be a location associated with server 16. As described previously, server 16 may represent a plurality of servers and, thus, it may have a first network location for receiving an electronic medical record and a second network location for serving and/or receiving the electronic signature. Alternatively, both functions may be served from a single network location. In another embodiment, server 16 may be configured to serve user interface features for operating a medical procedure using medical device 12 as well as operating an electronic signature user interface. In this embodiment, a second computer is not necessarily needed for performing the electronic signature function.

In this embodiment, medical device 12 may be configured to generate and transmit a medical record to server 16 using a first user interface operating from an embedded processor on device 12 and then, upon or after receiving confirmation that the medical record is stored in DBMS 14, to switch to a second user interface sourced from server 16 to provide electronic signature functionality. In response to a user entering credentials, device 12 may be configured to transmit the credentials to the server serving the web page. The credentials may then be verified as described in earlier embodiments. Use of a web page served from a remote server computer allows for easier modification of the user interface, since the server can be modified without having to modify or update software on a large number of medical devices. Use of a web page server also provides flexibility as to the runtime location of the client user interface, whether on the medical device or on a second computer.

In one embodiment, server 16 and medical device 12 communicate over a network, at least a portion of which is a wireless network. Server 16 will not initiate communication with medical device 12 (whether device 12 is an apheresis machine, infusion pump, or other medical device). Instead, medical device 12 will initiate any communications with server 16. Server 16 will only know medical device 12 is communicating with it when medical device 12 is communicating with it. Medical device 12 is configured to ignore any request to initiate a wireless communication session with medical device 12 made from a remote device. This embodiment provides an added level of security, to prevent remote control or communication with device 12 made by an unauthorized device.

Figure 4:
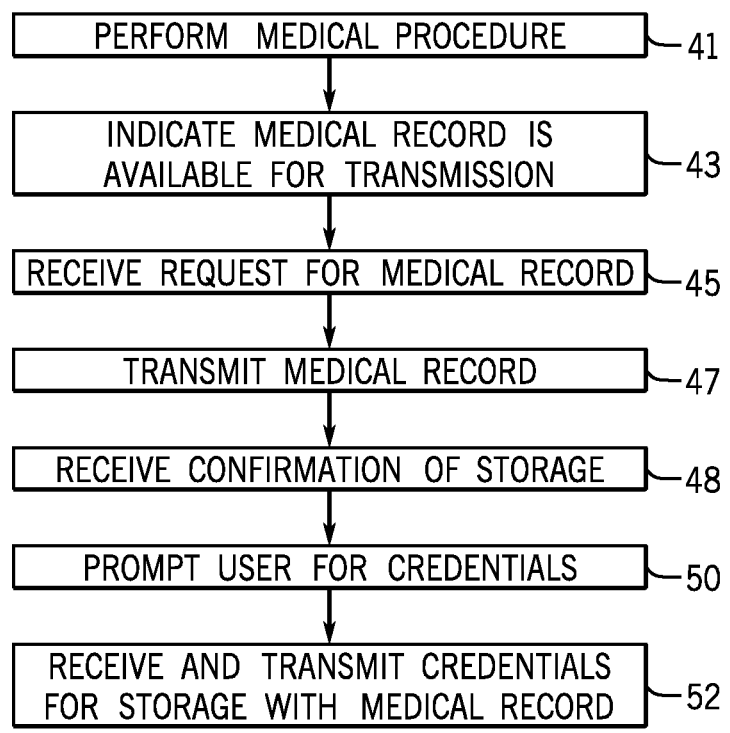
FIG. 4 is a flowchart illustrating a method of storing an electronic medical record with an electronic signature, according to an illustrative embodiment.

Referring now to FIG. 4, a flowchart illustrating a method of storing an electronic medical record with an electronic signature is shown, according to an illustrative embodiment. At a step 41, a medical device is configured to perform a medical procedure on a patient and to store data relating to the medical procedure in the form of a medical record. At a step 43, the medical device is configured to initiate a communication session with a remote server computer and to indicate that an electronic medical record is available for transmission. At step 45, a request is received from the remote server for the transmission of the medical record. At a step 47, the medical device is configured to transmit the medical record to the remote server.

At a step 48, the medical device is configured to receive a confirmation message from the server that the medical record has been stored in a database in accordance with at least one record storage criterion. At a step 50, the medical device is configured to prompt a user via a user interface to enter credentials suitable to electronically sign the document. At a step 52, credentials are received and transmitted to the remote server for verification and storage along with the medical record.

Advantageously, in the medical device described with reference to FIG. 4, the medical device need not have local storage sufficient to comply with one or more of the record storage criteria (such as a full set of government regulations).

While exemplary embodiments include components such as a HTTP server, DBMS, web browser, etc., the physical deployment is flexible in the choice of components, and as such any commercially available HTTP server (e.g. Apache, Internet Information Server (IIS), etc.) may be used in various embodiments, thus making the systems and methods portable across different deployment platforms. In addition, the systems and methods do not require a specific networking technology. In one embodiment, an HTTP protocol can be supported by underlying communication infrastructure. TCP/IP networking technology may be used to provide off-the-shelf security and integrity of communication.

The invention claimed is:

1. A system for storing an electronic medical record with an electronic signature in a database, comprising:
   an apheresis machine configured to perform an apheresis procedure on a patient, the apheresis machine configured to transmit an unsigned medical record; and
   a server computer comprising:
   a network interface circuit configured to provide communications over a network; and
   a processing circuit configured to:
      receive the unsigned medical record from the apheresis machine;
      generate a user interface screen configured to receive an electronic signature for the unsigned medical record;
      transmit the user interface screen to the apheresis machine over the network;
      receive an electronic signature entered using the user interface screen; and
      store the unsigned medical record and electronic signature in the database.

2. The system of claim 1, wherein the user interface screen is a web page based on hypertext transfer protocol served from the server computer.

3. The system of claim 1, wherein the processing circuit is configured to transmit the user interface screen to the apheresis machine.

4. The system of claim 1, wherein the processing circuit is configured to store the unsigned medical record in accordance with a plurality of record storage criteria for compliance with a government regulation governing electronic medical records.

* * * * *